US009474599B2

(12) United States Patent
Keränen

(10) Patent No.: US 9,474,599 B2
(45) Date of Patent: Oct. 25, 2016

(54) ARRANGEMENT, A LOOP-SHAPED SUPPORT, A PROSTHETIC HEART VALVE AND A METHOD OF REPAIRING OR REPLACING A NATIVE HEART VALVE

(71) Applicant: Medtentia International Ltd. Oy, Helsinki (FI)

(72) Inventor: Olli Keränen, Bjärred (SE)

(73) Assignee: MEDTENTIA INTERNATIONAL LTD OY, Helsinki (FI)

( * ) Notice: Subject to any disclaimer, the term of this patent is extended or adjusted under 35 U.S.C. 154(b) by 0 days.

(21) Appl. No.: 14/373,878

(22) PCT Filed: Jan. 24, 2013

(86) PCT No.: PCT/EP2013/051366
§ 371 (c)(1),
(2) Date: Jul. 22, 2014

(87) PCT Pub. No.: WO2013/110722
PCT Pub. Date: Aug. 1, 2013

(65) Prior Publication Data
US 2015/0039082 A1 Feb. 5, 2015

Related U.S. Application Data

(60) Provisional application No. 61/590,715, filed on Jan. 25, 2012.

(30) Foreign Application Priority Data

Jan. 24, 2012 (EP) .................................. 12152348

(51) Int. Cl.
*A61F 2/24* (2006.01)

(52) U.S. Cl.
CPC ........... *A61F 2/2409* (2013.01); *A61F 2/2418* (2013.01); *A61F 2/2427* (2013.01);
(Continued)

(58) Field of Classification Search
CPC .. A61F 2/2409; A61F 2/2466; A61F 2/2427; A61F 2/2418; A61F 2/2445; A61F 2/2442; A61F 2230/08; A61F 2230/0013; A61F 2230/0091; A61F 2250/006
See application file for complete search history.

(56) References Cited

U.S. PATENT DOCUMENTS

| 6,419,696 B1 * | 7/2002 | Ortiz | A61F 2/2445 623/2.37 |
| 7,717,955 B2 * | 5/2010 | Lane | A61F 2/2409 623/2.14 |

(Continued)

FOREIGN PATENT DOCUMENTS

| WO | WO 02/03892 A1 | 1/2002 |
| WO | WO 2004/030569 A2 | 4/2004 |
| WO | WO 2008/058940 A1 | 5/2008 |

OTHER PUBLICATIONS

WIPO, European International Search Authority, International Search Report mailed Aug. 19, 2013 in International Patent Application No. PCT/EP2013/051366, 7 pages.
(Continued)

*Primary Examiner* — Vy Bui
(74) *Attorney, Agent, or Firm* — Inskeep IP Group, Inc.

(57) ABSTRACT

The present disclosure relates to an arrangement, a loop-shaped support, a prosthetic heart valve and a method of repairing or replacing a native heart valve. With the method or the arrangement, leakage or regurgitation between a prosthetic heart valve and the surrounding valve tissue is prevented. In one embodiment, an arrangement for replacement or repair of a native heart valve is provided, which comprises a loop-shaped support (41) and a prosthetic heart valve (70) and wherein an outer segment (32) of the loop-shaped support (41) is positionable towards surrounding valve tissue of a native heart valve and wherein an outer surface (74) of the prosthetic heart valve (70) is positionable towards an inner segment (34) of the loop-shaped support (41) so as to prevent paravalvular leakage or regurgitation between the prosthetic heart valve (70) and the surrounding valve tissue of the native heart valve.

12 Claims, 6 Drawing Sheets

(52) U.S. Cl.
CPC .......... *A61F2/2442* (2013.01); *A61F 2/2445* (2013.01); *A61F 2/2466* (2013.01); *A61F 2230/008* (2013.01); *A61F 2230/0013* (2013.01); *A61F 2230/0091* (2013.01); *A61F 2250/006* (2013.01)

(56) References Cited

U.S. PATENT DOCUMENTS

2006/0195184 A1    8/2006    Lane et al.
2006/0195185 A1    8/2006    Lane et al.
2010/0030014 A1    2/2010    Ferrazzi
2010/0076549 A1    3/2010    Keidar et al.

OTHER PUBLICATIONS

WIPO, International Preliminary Examining Authority (European Patent Office), International Preliminary Report on Patentability mailed Oct. 28, 2014 in International Patent Application No. PCT/EP2013/051366, 12 pages.

* cited by examiner

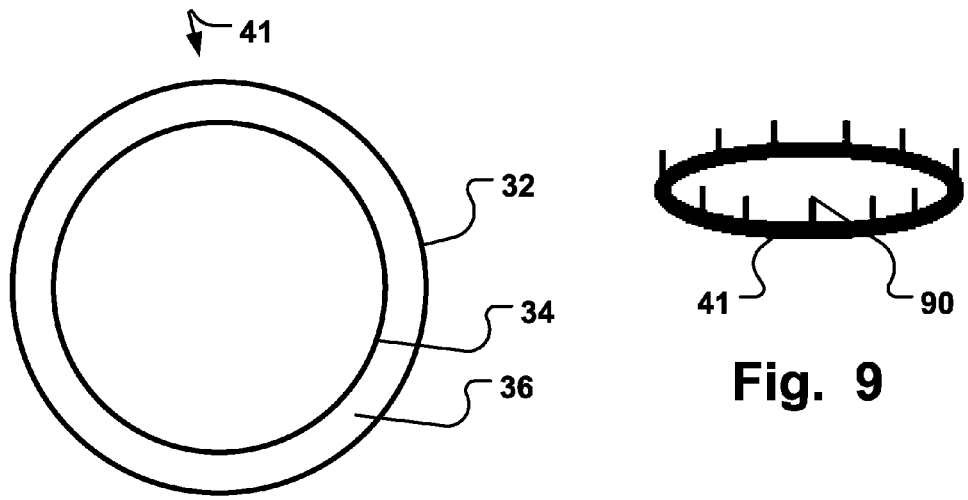
Fig. 3a
Fig. 9
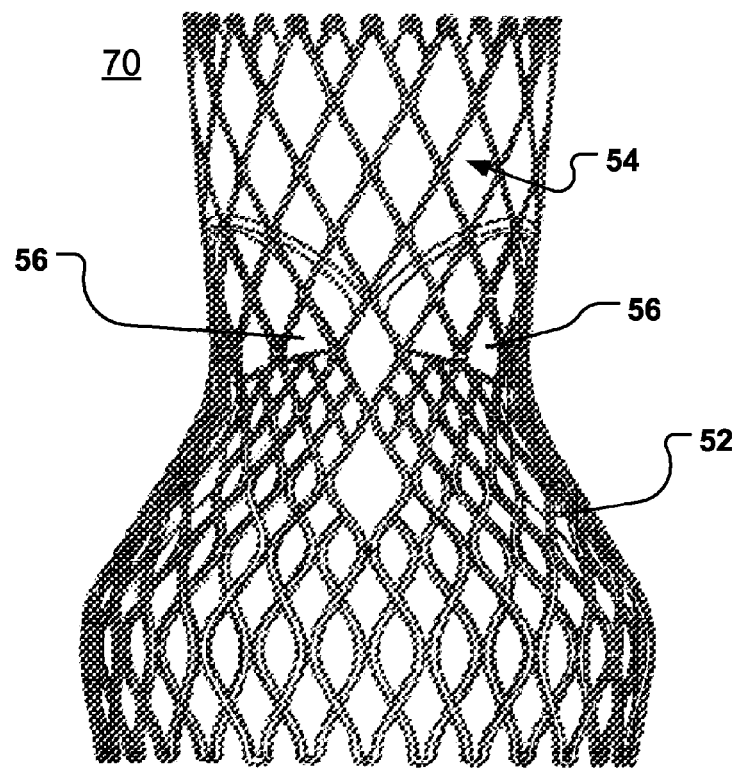
Fig. 6

ARRANGEMENT, A LOOP-SHAPED SUPPORT, A PROSTHETIC HEART VALVE AND A METHOD OF REPAIRING OR REPLACING A NATIVE HEART VALVE

RELATED APPLICATIONS

This application is the U.S. National Phase of and claims priority to International Patent Application No. PCT/EP2013/051366, International Filing Date Jan. 24, 2013, entitled An Arrangement, A Loop-Shaped Support, A Prosthetic Heart Valve And A Method Of Repairing Or Replacing A Native Heart Valve, which claims benefit of European Application No. EP12152348.4, filed Jan. 24, 2012 entitled An Arrangement, A Loop-Shaped Support, A Prosthetic Heart Valve And A Method Of Repairing Or Replacing A Native Heart Valve; and U.S. Provisional Application Ser. No. 61/590,715, filed Jan. 25, 2012 entitled An Arrangement, A Loop-Shaped Support, A Prosthetic Heart Valve And A Method Of Repairing Or Replacing A Native Heart Valve; all of which are incorporated herein by reference in their entireties.

BACKGROUND OF THE INVENTION

1. Field of the Invention

This disclosure pertains in general to the field of medical devices and methods. More particularly, the disclosure relates to a medical device for improving the function of a heart valve, and in particular to replacement or repair of a native heart valve.

2. Description of the Prior Art

In FIG. 1, a portion of the heart 12 is illustrated. The portion comprises the mitral valve 18, and the left ventricle 14. The mitral valve is at its boundary circumferenced by an annulus 20. The valve has two cusps or leaflets 22, 24. Each of these cusps or leaflets 22, 24 are connected to a respective papillary muscle 27, 29 via their respective connecting chordae 26, 28. In normal healthy individuals, the free edges of the opposing leaflets 22, 24 will close the valve. However, for some individuals the closure is not complete, which results in regurgitation, also called valvular insufficiency, i.e. a back flow of blood to the left atrium and potentially increasing blood pressure in pulmonary circulation making the heart less effective and with potentially severe consequences for the patient. FIG. 2 illustrates a mitral valve 18, in which the leaflets 22, 24 do not close properly. This commonly occurs when the annulus 20 becomes dilated. One surgical procedure to correct this is to remove a portion of the leaflet 24 and stitch the cut edges together with one another. The procedure will pull back the annulus 20 to a more normal position. However the strength of the leaflet 24 is altered. Similar problems with a less effective heart function may occur if one or both leaflets 22, 24 are perforated to such an extent that blood is flowing towards the left atrium, although the leaflets close properly.

In some conditions of degenerated heart function, the leaflets 22, 24 do not present a solid surface, as in a degenerative valve disease. The leaflet could also be perforated, with one or several holes, where the blood can flow backwards into the atrium.

Another possibility is that the leaflet is ruptured, most commonly at an edge of a leaflet, resulting in an incomplete coaptation. In some conditions of degenerated heart function, the leaflets do not present a solid surface, e.g. degenerative valve disease. The leaflet could be perforated, with one or several holes, where the blood can flow backwards into the atrium. Another possibility is that the leaflet is ruptured, most commonly at an edge of a leaflet, resulting in an incomplete coaptation.

Similar problems may arise in other native heart valves, such as in an aortic valve, in a pulmonic valve or in a tricuspid valve.

Some or all of these deficiencies may be remedied by the insertion of a prosthetic heart valve. However, it may be difficult to fit the prosthetic heart valve tightly to the native heart valve and thus, there may be a back-flow or leakage between the annulus or other surrounding valve tissue and the prosthetic heart valve.

Hence, an arrangement and/or a method for replacement or repair of a native heart valve, in which there is no paravalvular leakage or regurgitation between a prosthetic heart valve and the surrounding valve tissue, would be advantageous.

Furthermore, for fastening of such a prosthetic heart valve, replacement flaps can be used. Such replacement flaps can be anchored at dysfunctional flaps of the native heart valve and thereby give radial supporting force to the prosthetic heart valve, which is therefore also anchored. There is some prior art in this field, e.g. EP 1 994 913 A2; EP 1 469 797 B1; EP 1 259 195 B1; WO 2007/051620 A1; WO 2007/048529 A1; EP 1 980 220 A1; WO 01/64137 A1; EP 1 255 510 B3; U.S. Pat. No. 5,411,552 A and WO2008/058940 A1. From WO2008/058940 A1, a device for improving the function of a heart valve is known, which comprises a first loop-shaped support, which is configured to abut a first side of a heart valve, and a first flange unit being connected to the first loop-shaped support. The flange unit is configured to be arranged against the annulus when the first loop-shaped support is abutting the heart valve.

However, for a device, such as the one described in WO2008/058940 A1, it may be advantageous to provide for a prosthetic valve, which is positionable tightly towards a loop-shaped support.

Moreover, for a device, such as the one described in WO2008/058940 A1, it may be advantageous to improve support of the positioning of a prosthetic heart valve inside the loop-shaped support.

In addition, for a device, such as the one described in WO2008/058940 A1, it may be advantageous to seal the area between the prosthetic heart valve and a loop-shaped support.

SUMMARY OF THE INVENTION

Accordingly, embodiments of the present disclosure preferably seek to mitigate, alleviate or eliminate one or more deficiencies, disadvantages or issues in the art, such as the above-identified, singly or in any combination by providing an arrangement, a loop-shaped support, a prosthetic heart valve and a method of repairing or replacing a native heart valve, according to the appended patent claims.

According to aspects of the disclosure, an arrangement, a loop-shaped support, a prosthetic heart valve and a method of repairing or replacing a native heart valve are disclosed, whereby leakage or regurgitation between a prosthetic heart valve and the surrounding valve tissue is prevented.

According to a first aspect of the disclosure, an arrangement for replacement or repair of a native heart valve is provided. The arrangement comprises a loop-shaped support; and a prosthetic heart valve. An outer segment of the loop-shaped support is positionable towards surrounding valve tissue of the native heart valve. Furthermore, an outer surface of the prosthetic heart valve is positionable towards an inner segment of the loop-shaped support. The circumference of the loop-shaped support is substantially larger than a circumference of the prosthetic heart valve. The loop-shaped support is radially downsizeable to fit tightly around the prosthetic heart valve so as to seal the area between the prosthetic heart valve and the loop-shaped support. Thereby paravalvular leakage or regurgitation between the prosthetic heart valve and the surrounding valve tissue of the native heart valve is prevented. The native heart valve may be an aortic valve, a mitral valve, a pulmonic valve or a tricuspid valve. Thus, an atrioventricular valve prosthesis can be used for one or several of an aortic valve, a mitral valve, a pulmonic valve or a tricuspid valve.

According to a second aspect of the disclosure, a loop-shaped support is provided. The loop-shaped support is intended to be used in an arrangement for replacement or repair of a native heart valve. It has an inner segment and an outer segment. The inner segment is positionable towards a prosthetic heart valve and the outer segment is positionable towards surrounding valve tissue of a native heart valve. The circumference of the loop-shaped support is substantially larger than a circumference of the prosthetic heart valve. The loop-shaped support is radially downsizeable to fit tightly around the prosthetic heart valve so as to seal the area between the prosthetic heart valve and the loop-shaped support. Thereby paravalvular leakage or regurgitation between the prosthetic heart valve and the surrounding valve tissue is prevented.

According to a third aspect of the disclosure, a prosthetic heart valve is provided. The prosthetic heart valve is intended to be used in an arrangement for replacement or repair of a native heart valve. The prosthetic heart valve has an outer surface being positionable towards an inner segment of a loop-shaped support. The circumference of the loop-shaped support is substantially larger than a circumference of the prosthetic heart valve. The loop-shaped support is radially downsizeable to fit tightly around the prosthetic heart valve so as to seal the area between the prosthetic heart valve and the loop-shaped support. Thereby paravalvular leakage or regurgitation between the prosthetic heart valve and surrounding valve tissue is prevented.

According to a fourth aspect of the disclosure, a method of repairing or replacing a native heart valve is provided. The method comprises positioning of a loop-shaped support at an annulus of a native heart valve. The loop-shaped support comprises an inner segment and an outer segment. The outer segment of the loop-shaped support is positioned towards the annulus or surrounding valve tissue. Thereafter, a prosthetic heart valve is advanced towards the loop-shaped support. The prosthetic heart valve can be advanced partly through the loop-shaped support. An outer surface of the prosthetic heart valve is positioned towards the inner segment of the loop-shaped support. Thereby, paravalvular leakage or regurgitation between the prosthetic heart valve and the annulus and/or the surrounding valve tissue of the native heart valve is prevented.

Further embodiments of the disclosure are defined in the dependent claims, wherein features for the second and subsequent aspects of the disclosure are as for the first aspect mutatis mutandis.

Some embodiments of the disclosure provide for replacement or repair of a native heart valve.

Some embodiments of the disclosure provide for prevention of paravalvular leakage or regurgitation between the prosthetic heart valve and the surrounding valve tissue of the native heart valve.

Some embodiments of the disclosure also provide for sealing of the area between the prosthetic heart valve and the loop-shaped support to further improve prevention of paravalvular leakage or regurgitation.

Some embodiments of the disclosure also provide for that both the area between the surrounding valve tissue and the flange unit/loop-shaped support and the area between the prosthetic heart valve and the flange unit/loop-shaped support are sealed.

Some embodiments of the disclosure also provide for fixation of the loop-shaped support and/or the prosthetic heart valve.

Some embodiments of the disclosure also provide for improved stability.

Some embodiments of the disclosure also provide for prevention of unwanted loop-shaped support and prosthetic heart valve movement.

Some embodiments of the disclosure also provide for that valve tissue will be trapped between the supports to fixate a desired shape of the valve.

Some embodiments of the disclosure also facilitate delivery of a prosthetic heart valve.

Some embodiments of the disclosure also provide for enabling minimally invasive and percutaneous replacement or repair of cardiac valves.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the disclosure are capable of will be apparent and elucidated from the following description of embodiments of the present disclosure, reference being made to the accompanying drawings, in which

FIG. 3a is a top view of a loop-shaped support;

FIG. 6 is a lateral view of a stented prosthetic heart valve;

FIG. 9 is a view from above at an angle of a loop-shaped support equipped with fingers.

DESCRIPTION OF THE PREFERRED EMBODIMENTS

Figure 1:
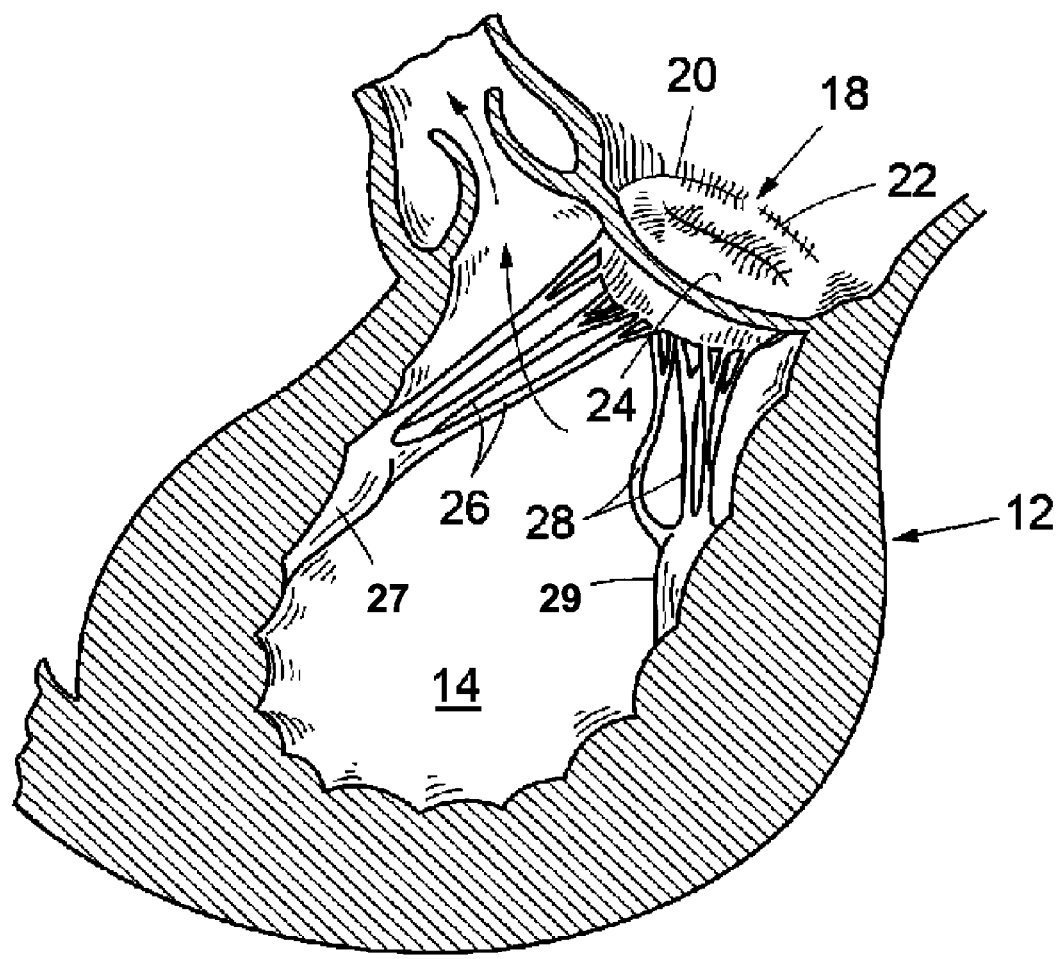
FIG. 1 is a cross-sectional view of the left ventricle of the heart.
Figure 2:
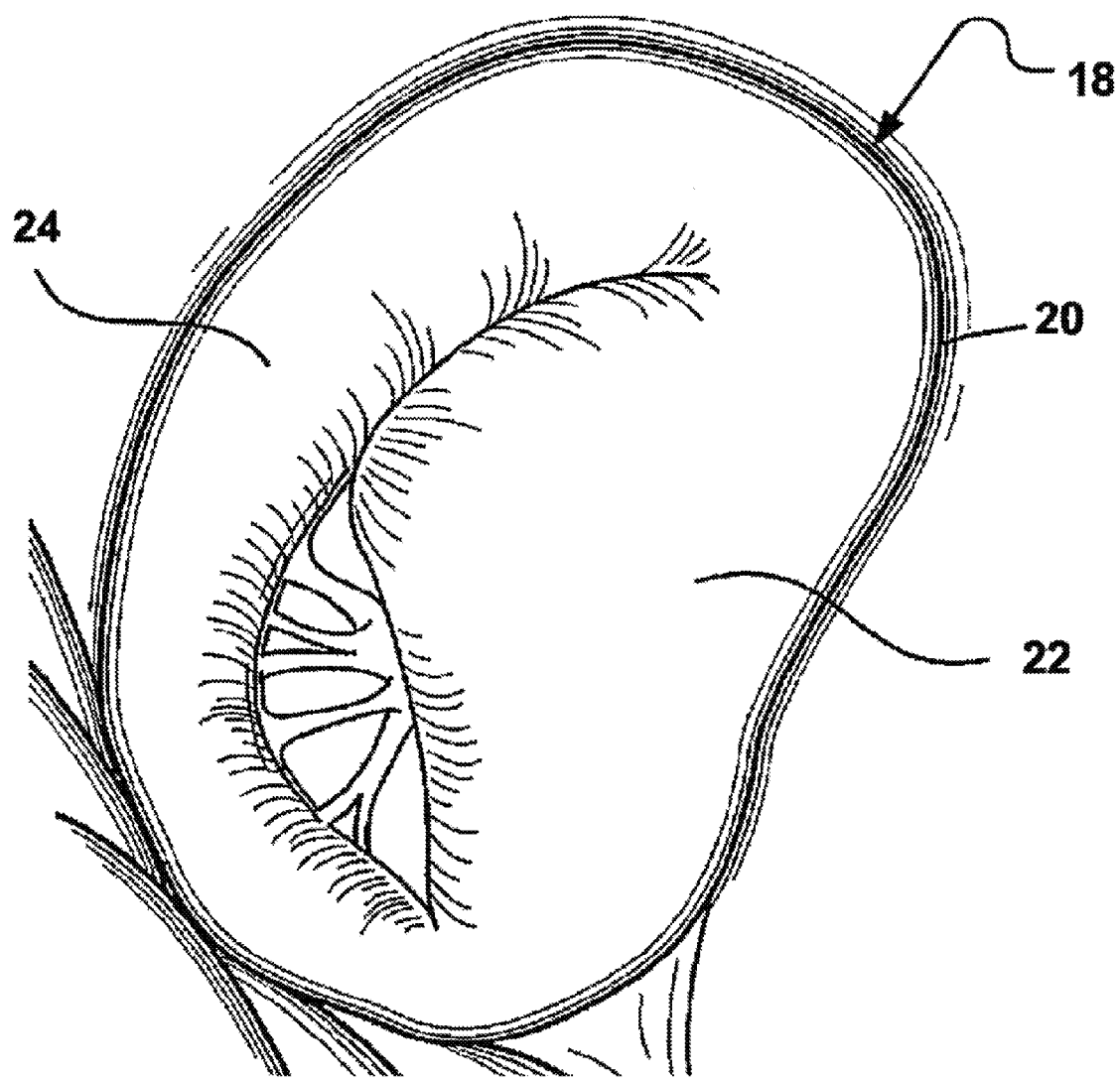
FIG. 2 is a lateral view of the mitral valve.

Specific embodiments of the disclosure will now be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the disclosure. In the drawings, like numbers refer to like elements.

The following description focuses on an embodiment of the present disclosure applicable to a native heart valve and in particular to a mitral valve. However, it will be appreciated that the disclosure is not limited to this application but may be applied to many other heart valves including for example an aortic valve, a pulmonic valve or a tricuspid valve.

In an embodiment of the disclosure according to FIG. 3a, the loop-shaped support 41 is round and forms a circle. The loop-shaped support 41 has an outer segment 32 and an inner segment 34. The outer segment 32 may on the outer edge of the loop-shaped support 41 be threaded so as to provide a possibility to better fixate the loop-shaped support to the surrounding valve tissue and thus prevent the loop-shaped support from sliding out of its position. As can be seen from FIG. 3a, the loop-shaped support 41 has a top portion 36 located between the outer segment 32 and the inner segment 34. On the opposite side of the top portion, there is a bottom portion (not seen in the figure).

Figure 3B:
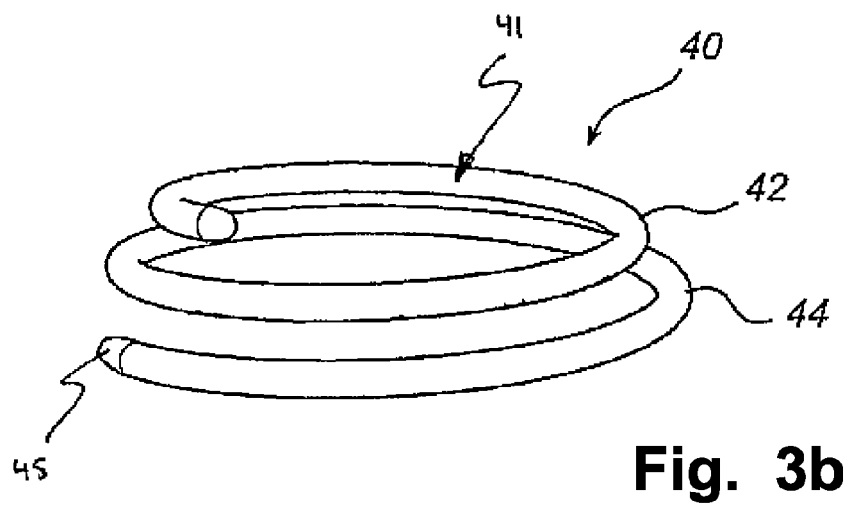
FIG. 3b is a lateral view of a helically shaped and loop-shaped support.
Figure 4:
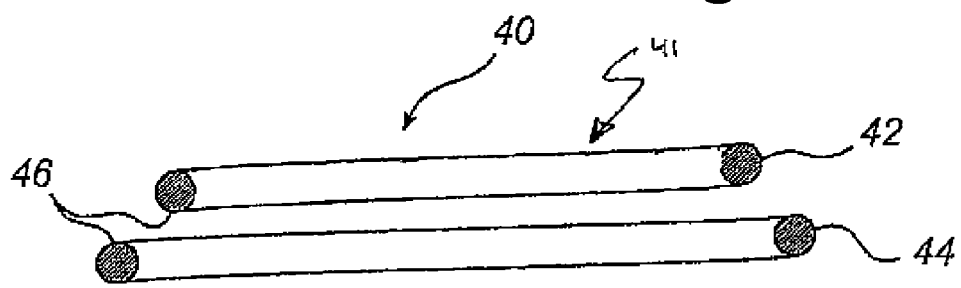
FIG. 4 is a cross-sectional view of a loop-shaped support.

Another loop-shaped support 41 according to one embodiment of the present disclosure is shown in FIGS. 3b and 4. The loop-shaped support 41 comprises a first and a second section 42, 44.

As used herein, the term "loop-shaped" should be construed as a curved shape that may be closed, as at least a part of a ring with e.g. a circular, elliptic, or D-shaped form or any other closed form which may fit the shape of the valve annulus. The term "loop-shaped" also includes a curved shape that is open forming an arcuate shape, such as a C-shape or U-shape, which includes an angular turn of at least 180° such that the support may abut valve tissue along a major part of the annular valve shape. The term "loop-shaped" also includes a curved shape overlapping itself to form a portion of a coil or helical structure. Such a helical structure may comprise a first part to be placed on the atrial side of the native heart valve and a second part to be placed on the ventricular side of the native heart valve. The first part may have a diameter, which is larger than a diameter of the second part. A helical loop-shaped support or helical support rings may also be used for anchoring of occlusion devices, such as occluders for closing atrial septal defects.

The term "loop-shaped" also includes three dimensional curves.

The loop shape of at least a part of at least one of the sections 42, 44 may also in some embodiments be patient configured. The shape may be designed specifically to an anatomy of a patient. The patient specific loop shape may be virtually derived from 3D patient data, e.g. acquired by image modalities, such as Magnetic Resonance (MR) or Computer Tomography (CT) Imaging.

In U.S. Pat. No. 6,419,696, U.S. Pat. No. 6,730,121, U.S. Pat. No. 6,964,684, and WO 2006/091163, which are assigned to the same applicant as the present disclosure and incorporated by reference herein in their entirety for all purposes, devices are disclosed for repairing and replacing a heart valve in various embodiments. The devices include at least first and second support rings connected together in loop-shaped configurations to abut opposite sides of a valve annulus. A replacement valve may be secured to the loop-shaped devices.

The first section 42 may be continuous and/or integral with the second section 44 such that the sections 42, 44 assume a coiled configuration in the form of a spiral or key ring-type configuration with two loops.

The second section 44 may have an outer boundary or extent which is greater in relation to the outer boundary of the first section 42. The sections 42, 44 may in an embodiment have corresponding shapes with the second section 44 being in larger scale than the first section 42. This is advantageous for creating a pinch of the valve tissue between the first 42 and second sections 44.

An end 45 of the second section 44, which will lead the coil during insertion of the device at the valve, may in an embodiment have a greater pitch than the rest of the coil. This implies that the leading end 45 of the coil during rotation into position in the valve will project from immediate contact with the valve tissue and, therefore, the risk that the coil is caught by the chords is diminished.

The loop-shaped support 41 is shown in cross-section in FIG. 4. The loop-shaped support 41 has in an embodiment at least partly a round cross-sectional shape. In other embodiments, the cross-section of the loop-shaped support 41 may be substantially flat, oval, flattened and/or have flattened edges. As an example, the loop-shaped support 41 may in one embodiment have an outer segment 32, which is substantially round or rounded and an inner segment 34, which is substantially flat or flattened. A better fit to a prosthetic heart valve may be provided by the use of a flat or flattened inner segment 34. Thereby, the sealing of the area between the prosthetic heart valve and the loop-shaped support and the prevention of paravalvular leakage is further improved.

In embodiments, the opposed surfaces 46 thus provide a pinch to trap valve tissue there between. A round cross-section is also advantageous in creating a pinch of the valve tissue which will not harm the leaflets in their movement during normal heart action.

The second section 44 is slightly displaced radially with respect to the first section 42. This implies that the first and second sections 42, 44 are not arranged directly on top of each other in some embodiments. The pinch between the first 42 and second sections 44 is therefore not sharply defined in a radial direction of the valve. This implies that a pinching force between the sections 42, 44 is not focused to a specific radial position of the valve. As a result, the pinching force does not affect the movement of the leaflets during normal heart action and there is a diminished risk of rupture in the leaflets at the pinch.

The sections 42, 44 may in some embodiments be interrelated in such a manner that the outer boundary of the first section 42 has a diameter corresponding to a line through the centre of the second section 44. Thus, the sections 42, 44 may overlap somewhat such that tissue is not allowed to move through the pinch and the shape of the valve is maintained advantageously.

Further, the cross-section of the sections 42, 44 is substantially round, which also gives a soft contact between the sections and the valve tissue to further diminish the risk of rupture in the leaflets.

The loop-shaped support 41 may be formed from a core of a rigid material, such as a metal, e.g. titanium, or plastic. The rigid material may provide a passive spring function, so that the loops of the coil may be forced a small distance away from each other but will flex back towards each other when the force is released. The core of the loop-shaped support 41 may be coated by a softer layer, such as a textile.

The loop-shaped support 41 may alternatively be formed from a shape memory material. The loop-shaped support 41 will then assume a desired, programmed shape, when e.g.

heated to a specific temperature. This allows the loop-shaped support 41 to be compressed or straightened to a form better suited for deliverance and/or during insertion and to assume a spiral or helical shape when inserted at the heart valve. Also a flange unit 50 may be made of such a shape memory material, e.g. to provide a first, delivery shape and a second shape assumed after being delivered.

Figure 5:
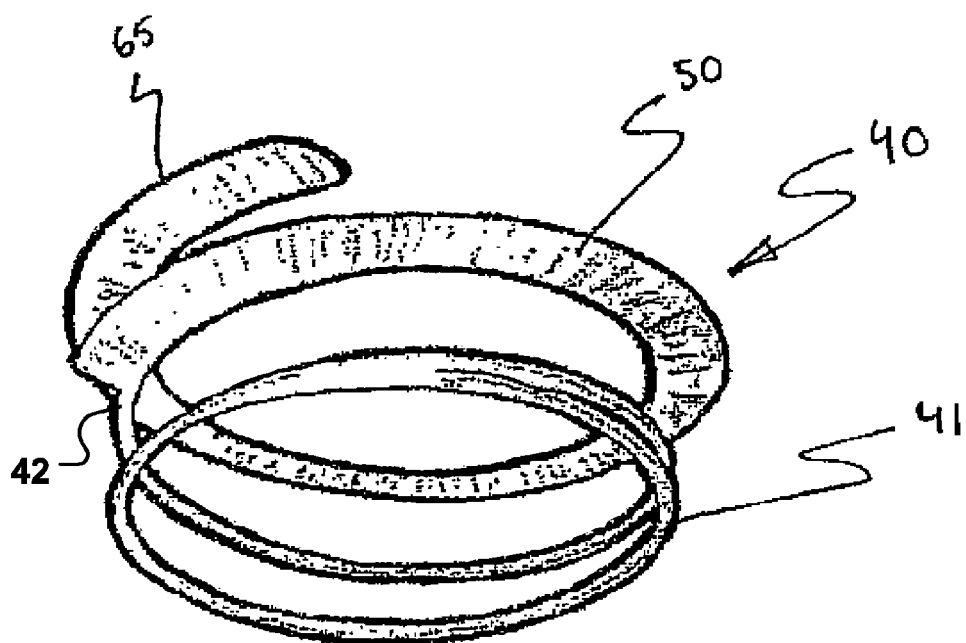
FIG. 5 is a lateral view of a loop-shaped support with a flange unit.

Now turning to FIG. 5, an embodiment of the loop-shaped support 41 is disclosed. The loop-shaped support 41 comprises a flange unit 50 being connected to the first section 42. The flange unit 50 has in an embodiment a continuous extension along the periphery of the first section 42.

In some embodiments, the flange unit 50 may be integral with at least a portion of the loop-shaped support 41.

In some embodiments the flange unit 50 is made of a tube shaped flexible material being passed onto the first section 42, whereby a loose substantially co-axial connection between the loop-shaped support 41 and the flange unit 50 is achieved. The connection may also be fixed or rigid. The flexible material may by way of example be a fabric or woven structure made of Polyethylene (PE) or polytetrafluoroethylene (PTFE). A fabric has the advantage that it presents a rough, holed or porous surface enhancing growth of and overgrowth of endothelia. Further, a fabric is easily penetrated by sutures or clips. In addition, the flexible material admits the flange unit 50 to be conformed to the annulus. It also admits the flange unit 50 to be conformed to a prosthetic heart valve 70.

The flange unit 50 does in the disclosed embodiment form a flange surface extending downwards out from the body. More precisely the flange unit 50 forms in some embodiments an angle α to a horizontal, diametric plane formed by the loop-shaped support. The angle α is approximately between 30-60°, such as 40-50° to the diametric plane. Such angle improves the visibility during insertion of the loop-shaped support. In some embodiments, improved visibility may be provided during insertion of the loop-shaped support, whereupon the flange unit 50 changes shape to a position facilitating fixation thereof to surrounding tissue. Thus, medical procedures for heart valve repair and/or replacement may be speeded up considerably.

In a practical embodiment the flange surface has a width in the range of approximately 2-4 mm, such as 2.5-3.5 mm. The width of the flange radially outwards allows an indication for the surgeon of the area in which sutures or clips should be positioned when fixating the loop-shaped support to the annulus. Initially, before inserted into the heart valve, the flange surface extends downwardly. When positioned in the atrial side of the heart valve, the loop-shaped support 41 will be arranged abutting the annulus, whereby the flange unit 50 will be conformed to the annulus, changing its angle from extending downwardly to extending upwardly. This ability to conform is a combination of the flexibility of the (fabric) material and the width of the flange unit 50.

On its outer periphery, the flange unit 50 may comprise a reinforcing element 65, which is schematically illustrated in FIG. 5. Such reinforcing element may by way of example have the form of a thread or a bead.

In an embodiment according to FIG. 6, a prosthetic heart valve 70 comprises a stent or stent frame 52 and a valve structure 54. The stent frame 52 is generally constructed so as to be self-expandable from a compressed arrangement to the normal, expanded arrangement (shown in FIG. 6). In other embodiments, the stent frame 52 is expandable to the expanded arrangement by a separate device, e.g., a balloon internally located within the stent frame 52. The valve structure 54 is assembled to the stent frame 52 and provides two or more leaflets 56. The prosthetic heart valve 70 may also be fastened as described in e.g. U.S. Pat. No. 5,411,552 A or EP1255510 B. As an example, a mitral valve or a tricuspid valve from e.g. a pig can be fastened to the loop-shaped support by sewing. The prosthetic heart valve 70 is configured for replacing or repairing a native mitral valve. Alternatively, other shapes are also envisioned, adapted to the specific anatomy of the valve to be repaired, e.g., stented prosthetic heart valves in accordance with the present disclosure can be shaped and/or sized for replacing a native aortic, pulmonic, or tricuspid valve. In one embodiment, the valve structure 54 extends less than the entire length of the stent frame 52, but in other embodiments it can extend along an entirety, or a near entirety, of a length of the stent frame 52. A wide variety of other constructions are also acceptable and within the scope of the present disclosure. For example, the stent frame 52 can have a more cylindrical shape in the normal, expanded arrangement.

Figure 7:
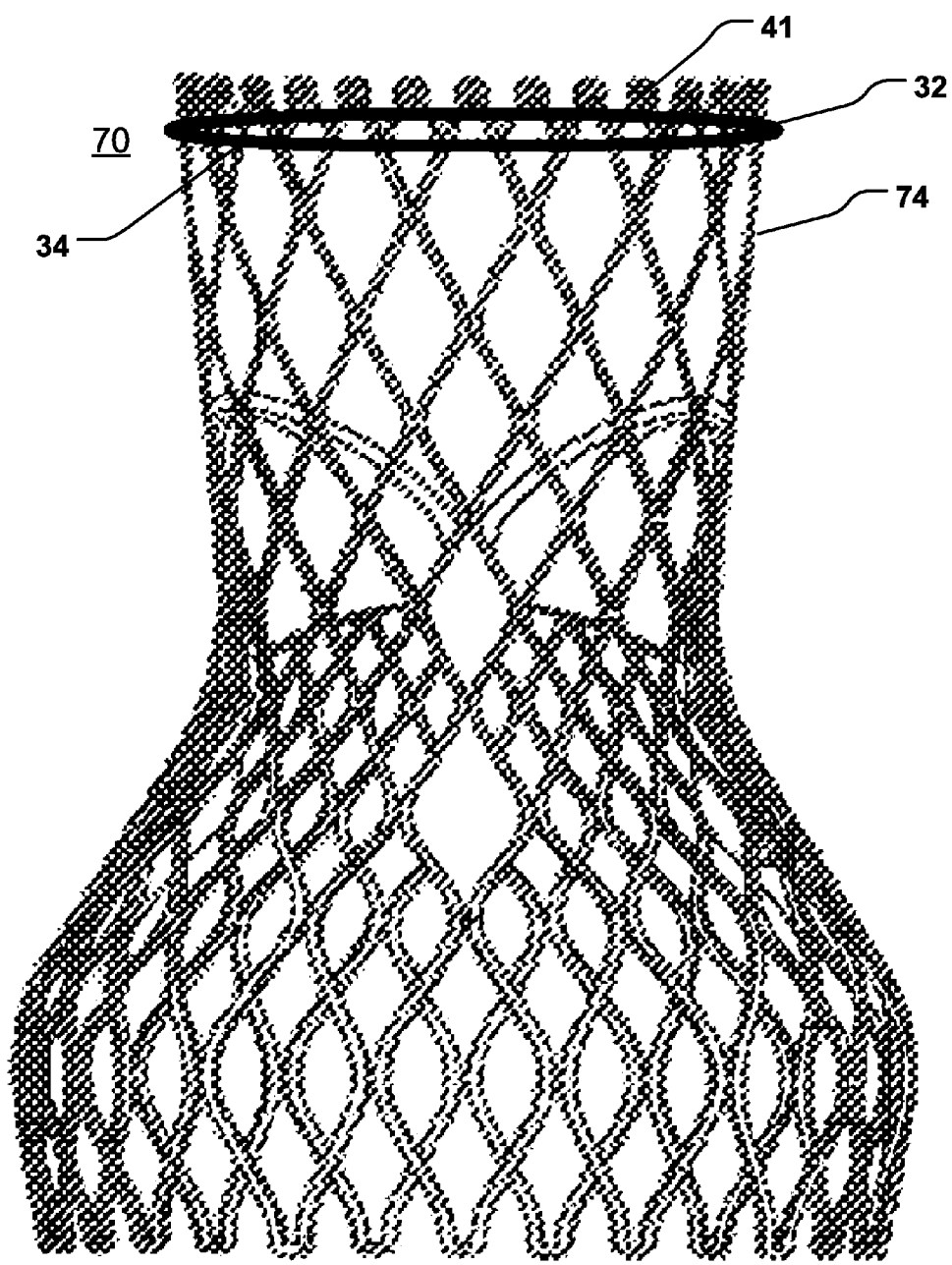
FIG. 7 is a lateral view of a stented prosthetic heart valve positioned inside a loop-shaped support.

A further embodiment of the disclosure is illustrated in FIG. 7. In FIG. 7, the prosthetic heart valve 70 is shown in an arrangement for replacement or repair of a native heart valve, together with a loop-shaped support 41. An outer segment 32 of the loop-shaped support 41 is positionable towards surrounding valve tissue of a native heart valve. Furthermore, as can be seen from the figure, an outer surface 74 of the prosthetic heart valve 70 is positionable towards an inner segment 34 of the loop-shaped support 41 so as to prevent paravalvular leakage or regurgitation between the prosthetic heart valve 70 and the surrounding valve tissue of the native heart valve. The inner segment 34 is adapted for receiving a radially expandable prosthetic heart valve 70, and the loop-shaped support 41 is radially rigid, i.e. rigid in a radial direction, for preventing an expansion of the prosthetic heart valve 70 beyond the inner segment 34. However, the expandable prosthetic heart valve 70 will expand as far as it can in order to reach its normal expanded state, when it is expanded during delivery. Thus, the outer surface 74 of the prosthetic heart valve 70 will be tightly positioned towards an inner segment 34 of the loop-shaped support 41. Thereby the area between the prosthetic heart valve 70 and the loop-shaped support 41 is sealed. In FIG. 7, the loop-shaped support 41 is depicted as a round circle-shaped support. However, in other embodiments, the loop-shaped support 41 may be helically or coil-shaped as depicted in FIGS. 3b-5.

Since the flange unit 50 provides for a sealing surface against the annulus allowing prevention of backflow of blood from the ventricle to the atrial side, both the area between the surrounding valve tissue and the flange unit 50/loop-shaped support 41 and the area between the prosthetic heart valve 70 and the flange unit 50/loop-shaped support 41 are sealed. The flange unit 50 may also form a flange surface on both sides of the annulus or heart valve, which surface may provide for fixation of loop-shaped support 41 and/or prosthetic heart valve 70.

Figure 8:
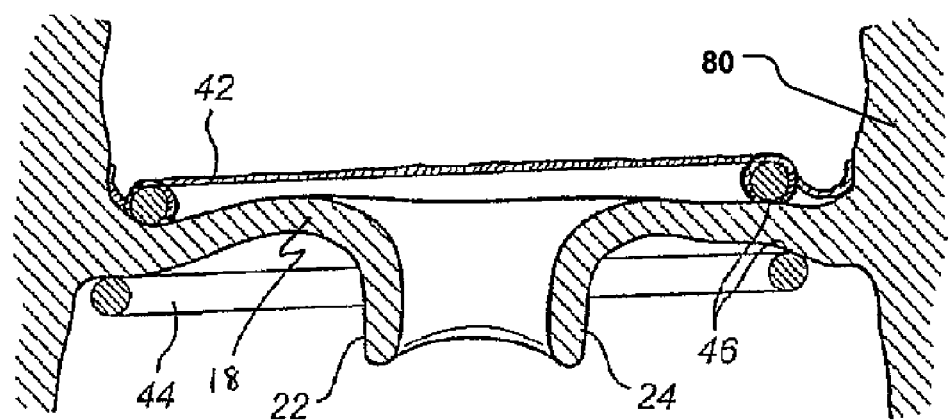
FIG. 8 is a lateral view of a loop-shaped support positioned at the target site before the stented prosthetic heart valve has been positioned inside the loop-shaped support.

FIG. 8 shows a loop-shaped support 41 positioned at the target site before the stented prosthetic heart valve 70 has been positioned inside the loop-shaped support 41. In this embodiment, the target site is a native heart valve, such as a mitral valve 18 and the loop-shaped support 41 is helically shaped. Also native leaflets 22, 24 and surrounding valve tissue 80 can be seen in the figure. The first and second sections 42, 44 are situated on either side of the valve, since the second section 44 has been rotated or screwed through the valve into its position. If needed, the loop-shaped support 41 may be further secured to the valve by clips, sutures or other suitable means.

In one embodiment, one of the sections, e.g. the first section 42 extends further away from the native heart valve than the other section, e.g. the second section 44, so as to provide a larger sealing area towards the prosthetic heart valve 70. Normally the loop-shaped support 41 is positioned at the target site first and first thereafter the prosthetic heart valve 70 is positioned at the target site. However, it is also possible that the prosthetic heart valve 70 is positioned at the target site before introduction of the loop-shaped support 41. When the loop-shaped support 41 has been positioned at the target site, the stented prosthetic heart valve 70 is fitted to the loop-shaped support 41 by first positioning the stented prosthetic heart valve 70 inside the loop-shaped support 41 and then expanding the stented prosthetic heart valve 70 to its normal expanded state. Thus, the area between the prosthetic heart valve 70 and the loop-shaped support 41 is sealed. Thereby paravalvular leakage or regurgitation between the prosthetic heart valve 50 and surrounding valve tissue is prevented.

A further embodiment is depicted in FIG. 9. Instead or in addition to having a section extending further away from the native heart valve, the loop-shaped support 41 may have fingers 90, extensions, crown-shaped extensions or struts connected to a top portion 36 or a bottom portion of the loop-shaped support 41 and pointing in a direction away from the native heart valve when the loop-shaped support 41 has been placed in its operational position, which direction is substantially parallel with a longitudinal centre axis of the loop-shaped support 41. These fingers may support the positioning of a prosthetic heart valve inside the loop-shaped support 41 and eliminate or reduce tilting movement in relation to a plane being in parallel with a mitral plane, i.e. a plane having the atrium on one side and the ventricle on the other side. The fingers 90 may be slightly flexible so that they can better adapt to the shape of a prosthetic heart valve. As an alternative, the loop-shaped support 41 may have fingers 90 extending in both directions pointing away from the native heart valve, i.e. in a direction from the native heart valve towards the atrium and in a direction from the native heart valve towards the ventricle, when the loop-shaped support has been placed in its operational position. By the use of fingers 90 in both directions, the positioning of a prosthetic heart valve inside the loop-shaped support may be further supported and thus, a tilting movement may be further reduced. In one embodiment, the loop-shaped support 41 has a top portion 36 and a bottom portion. At least one of the top 36 and bottom portions is connected to at least one crown-shaped portion and a top of the at least one crown-shaped portion is extending substantially perpendicularly towards the atrium or the ventricle so that the positioning of a prosthetic heart valve inside the loop-shaped support 41 is supported by the at least one crown-shaped portion. A tilting movement in relation to a plane being in parallel with a mitral plane may also be eliminated or reduced.

In some embodiments the prosthetic heart valve 70 is rigid. The outer surface 74 of the prosthetic heart valve 70 is tightly positioned towards the inner segment 34 of the loop-shaped support 41, so as to seal the area between the prosthetic heart valve 70 and the loop-shaped support 41. The loop-shaped support 41 is in these embodiments somewhat flexible to compensate for the rigidity of the prosthetic heart valve 70.

In some embodiments a circumference of the loop-shaped support 41 is substantially larger than a circumference of the prosthetic heart valve 70. The loop-shaped support 41 is then radially downsizeable to fit tightly around the prosthetic heart valve 70 so as to seal the area between the prosthetic heart valve 70 and the loop-shaped support 41. The loop-shaped support 41, which has a circumference which is substantially larger than the circumference of the prosthetic heart valve 70 may be downsizeable, e.g. by first assuming a first shape and then after positioning assuming a second shape, which may be obtained by a change of shape, such as a change of shape of a shape memory material. By such a change in shape, i.e. a change from oversized to a size that is just right, the loop-shaped support 41 may fit tightly around the prosthetic heart valve 70 so as to seal the area between the prosthetic heart valve 70 and the loop-shaped support 41. When the loop-shaped support 41 has assumed a size that is just right to fit tightly around the prosthetic heart valve 70, a force which is appropriate for sealing the area between the prosthetic heart valve 70 and the annuloplasty ring 41, but not large enough to cause any damage to the annuloplasty ring 41 or the native valve is exerted on the annuloplasty ring 41.

Another situation when valve leakage, i.e. regurgitation or valvular insufficiency may occur is during catheter-based delivery. During delivery through a catheter, e.g. for replacement or repair of cardiac valves, such as the mitral valve, there is a chance that the catheter delivered valve may cause leakage or regurgitation, since the surrounding tissue is non-rigid. The soft tissue in the annulus region is thus not tightly holding the valve in its desired place. The surrounding soft tissue may over extend and due to increasing blood pressure during the heart cycle, an outer by-pass blood flow may occur at the outer circumference of the valve or its casing or anchoring stent. In such a situation, a loop-shaped support 41 may be beneficial for preventing paravalvular leakage or regurgitation.

In some embodiments, the fingers 90 are slightly offset from the loop-shaped support 41 in a radial direction, so that there is a gap between the outer segment 32 of the loop-shaped support 41 and the fingers 90. The fingers 90 may then be attached to only a portion of the full axial length of the loop-shaped support 41 so that a gap is formed between the loop-shaped support and the fingers 90 for a part of the loop-shaped support in an axial direction. In one embodiment, the fingers are attached to the loop-shaped support 41 for at least half of the full axial length of the loop-shaped support 41. By the use of fingers 90, which are located slightly offset from the loop-shaped support, biological material, e.g. natural remaining valvular tissue from the native heart valve, such as dysfunctional flaps and/or chordae, can be trapped in the gap between the loop-shaped support 41 and the fingers 90. Thereby, the positioning of the loop-shaped support 41 and/or the prosthetic heart valve 70 is further stabilized and therefore paravalvular leakage is further prevented.

Also when metal is put against metal at a target site, such as at a mitral valve, there is no good adherence. Thus, there is a possibility of leakage or regurgitation between two metal parts, especially between two round or cylinder-formed metal parts or when one metal part is to be positioned inside another metal part. In one embodiment, a loop-shaped support 41 may be positioned in-between the metal parts at a target site, such as the mitral valve, so as to provide good adherence and to seal the area between the two metal parts, so that no leakage will occur at the target valve.

The arrangement, the loop-shaped support 41 and/or the prosthetic heart valve 70 can be implanted via a catheter. This may be performed transseptally, transapically or transvascularly, e.g. retroversily via the aorta.

Furthermore, other means, such as hooks, can be used for anchoring of the arrangement, the loop-shaped support 41 and/or the prosthetic heart valve 70. In one embodiment, the prosthetic heart valve 70 is anchored with anchor elements. Thus, a method of anchoring a prosthetic heart valve 70 in a patient's heart is provided. The method comprises anchoring the prosthetic heart valve 70 on the ventricular side with three or more, preferably four, anchor elements integrated with the prosthetic heart valve 70 situated on the ventricle side of the prosthetic heart valve 70, extending outwards from the prosthetic heart valve 70 and distributed equally around the prosthetic heart valve 70. The method further comprises anchoring the prosthetic heart valve 70 on the atrial side with three or more, preferably four, anchor elements integrated with the prosthetic heart valve 70 situated on the atrium side of the prosthetic heart valve 70, extending outwards from the prosthetic heart valve 70 and distributed equally around the prosthetic heart valve 70. By the use of this method, the prosthetic heart valve 70 is further stabilized in its position at the target site.

The present disclosure has been described above with reference to specific embodiments. However, other embodiments than the above described are equally possible within the scope of the disclosure. Different method steps than those described above, may be provided within the scope of the disclosure. The different features and steps of the disclosure may be combined in other combinations than those described. The scope of the disclosure is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

The invention claimed is:

1. An arrangement for replacement or repair of a native heart valve, comprising:
    a loop-shaped support that, after delivery to a target site, has a helical shape comprising a first loop and a second loop each positioned in substantially different diametric planes, a first shape assumed by the support having a first diameter and a second programmed shape assumed by the support having a second diameter smaller than the first diameter; and
    a radially expandable prosthetic heart valve, that after delivery to a target site, is positioned through the first loop and the second loop of the support, the first diameter of the support substantially larger than a diameter of the prosthetic heart valve and the second diameter of the support sized to fit tightly around an exterior of the prosthetic heart valve so as to seal the area between the prosthetic heart valve and the loop-shaped support.

2. The arrangement of claim 1, wherein said prosthetic heart valve is a stented prosthetic heart valve.

3. The arrangement of claim 2, wherein said surrounding valve tissue comprises an annulus, and wherein said arrangement further comprises a flange unit, said flange unit being connected to said loop-shaped support, and which flange unit is configured to be arranged against said annulus for attaching said flange unit and said loop-shaped support to said annulus and wherein said flange unit is of a fabric material.

4. The arrangement of claim 1 wherein the arrangement is configured to pinch native heart tissue between the first loop and the second loop of the support.

5. The arrangement of claim 1 wherein the arrangement is configured to pinch native heart tissue between the second loop of the support and the prosthetic heart valve.

6. The arrangement of claim 1 wherein a diameter of the first loop of the support is different from a diameter of the second loop of the support.

7. An arrangement for replacement or repair of a native heart valve comprising:
    a loop-shaped support that, after delivery to a target site, has a helical shape comprising a first loop and a second loop each positioned in a substantially different diametric plane, a first shape assumed by the support having a first diameter and a second programmed shape assumed by the support having a second diameter smaller than the first diameter; and
    a prosthetic heart valve, that after delivery to a target site, is positioned entirely through the first loop and the second loop of the support, the first diameter of the support substantially larger than a diameter of the prosthetic heart valve and the second diameter of the support sized to fit tightly around an exterior of the prosthetic heart valve so as to seal the area between the prosthetic heart valve and the loop-shaped support.

8. The arrangement of claim 7, wherein said surrounding valve tissue comprises an annulus, and wherein said arrangement further comprises a flange unit, said flange unit being connected to said loop-shaped support, and which flange unit is configured to be arranged against said annulus for attaching said flange unit and said loop-shaped support to said annulus and wherein said flange unit is of a fabric material.

9. The loop-shaped support of claim 7, wherein said loop-shaped support has fingers extending from a top and/or bottom portion of said loop-shaped support away from said loop-shaped support in a direction substantially parallel with a center axis of said loop-shaped support for supporting the positioning of a prosthetic heart valve inside said loop-shaped support.

10. The arrangement of claim 7 wherein the arrangement is configured to pinch native heart tissue between the first loop and the second loop of the support.

11. The arrangement of claim 7 wherein the arrangement is configured to pinch native heart tissue between the second loop of the support and the prosthetic heart valve.

12. The arrangement of claim 7 wherein a diameter of the first loop of the support is different from a diameter of the second loop of the support.

* * * * *